(12) United States Patent
Zhan et al.

(10) Patent No.: US 12,007,318 B2
(45) Date of Patent: Jun. 11, 2024

(54) DEVICE AND METHOD FOR IN SITU PENETRATION MEASUREMENT OF GAS TRANSPORT PARAMETERS IN UNSATURATED SOIL LAYER

(71) Applicant: ZHEJIANG UNIVERSITY, Zhejiang (CN)

(72) Inventors: Liangtong Zhan, Zhejiang (CN); Tao Wu, Zhejiang (CN); Song Feng, Zhejiang (CN); Yunmin Chen, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 350 days.

(21) Appl. No.: 17/639,909

(22) PCT Filed: Jun. 19, 2020

(86) PCT No.: PCT/CN2020/096943
§ 371 (c)(1),
(2) Date: Apr. 8, 2022

(87) PCT Pub. No.: WO2021/042813
PCT Pub. Date: Mar. 11, 2021

(65) Prior Publication Data
US 2022/0334041 A1 Oct. 20, 2022

(30) Foreign Application Priority Data
Sep. 3, 2019 (CN) .......................... 201910828573.6

(51) Int. Cl.
*G01N 13/04* (2006.01)
*G01N 15/08* (2006.01)

(52) U.S. Cl.
CPC ......... *G01N 13/04* (2013.01); *G01N 15/0826* (2013.01)

(58) Field of Classification Search
None
See application file for complete search history.

(56) References Cited

U.S. PATENT DOCUMENTS 5,332,333 A * 7/1994 Bentley ................... B09C 1/005
405/128.2

FOREIGN PATENT DOCUMENTS

| CN | 102288528 | 12/2011 |
| CN | 103061321 | 4/2013 |

(Continued)

OTHER PUBLICATIONS

"International Search Report (Form PCT/ISA/210) of PCT/CN2020/096943," mailed on Sep. 21, 2020, with English translation thereof, pp. 1-4.

(Continued)

*Primary Examiner* — Brandi N Hopkins
*Assistant Examiner* — Nigel H Plumb
(74) *Attorney, Agent, or Firm* — JCIPRNET (57) ABSTRACT

A device and a method for in situ penetration measurement of gas transport parameters in an unsaturated soil layer. The device mainly consists of a gas supply system, a gas concentration display recorder, a gas pressure display recorder, a sleeve, a gas concentration sensor, a gas pressure sensor, a porous gas-permeable tube and a conical penetration head. The gas diffusion coefficient and permeability coefficient of the unsaturated soil can be obtained by only measuring the gas pressure value, the gas concentration value and the corresponding gas flow value of an unsaturated soil layer at a depth required to be tested, and substituting same into calculation formulae of the gas diffusion coefficient and permeability coefficient. The testing process of the method is simple and fast, and is low in cost, simple in operation and convenient in calculation.

10 Claims, 2 Drawing Sheets

(56) References Cited

FOREIGN PATENT DOCUMENTS

| CN | 103115843 |   | 5/2013  |
|----|-----------|---|---------|
| CN | 109883892 |   | 6/2019  |
| CN | 110455673 | * | 11/2019 |

OTHER PUBLICATIONS

"Written Opinion of the International Searching Authority (Form PCT/ISA/237) of PCT/ CN2020/096943," mailed on Sep. 21, 2020, pp. 1-5.

* cited by examiner

DEVICE AND METHOD FOR IN SITU PENETRATION MEASUREMENT OF GAS TRANSPORT PARAMETERS IN UNSATURATED SOIL LAYER

CROSS-REFERENCE TO RELATED APPLICATION

This application is a 371 of international application of PCT application serial no. PCT/CN2020/096943, filed on Jun. 19, 2020, which claims the priority benefit of China application no. 201910828573.6, filed on Sep. 3, 2019. The entirety of each of the above mentioned patent applications is hereby incorporated by reference herein and made a part of this specification.

TECHNICAL FIELD

The disclosure belongs to the technical field of environmental geotechnical engineering, and in particular, relates to a device and a method for in situ testing of the gas diffusion coefficient and permeability coefficient of a soil body in an unsaturated soil layer.

DESCRIPTION OF RELATED ART

The gas diffusion coefficient and permeability coefficient are important indicators for determining the transport of gas in the soil layer, which are mainly affected by factors such as soil structure and its changes, pore tortuosity, pore size, and saturation. The soil cover is an important part of the closure and cover system of solid waste landfills. The gas diffusion coefficient and permeability coefficient are important parameters for the analysis and design of gas transport in the cover and play an important role in the emission reduction of greenhouse gases and harmful gases in the landfills. The soil cover is distributed over a large area. Due to the influence of factors such as drying-wetting cycles, construction technology, and uneven soil quality, soil gas diffusion coefficient and permeability coefficient exhibit spatial variability, which also leads to the differences between the testing results of the gas diffusion coefficients and permeability coefficients of the unsaturated soil measured in the laboratory and measured on site. Therefore, the invention of a device and a method that may accurately and quickly measure the soil gas diffusion coefficient and permeability coefficient at different depths of unsaturated soil in situ is of great significance for the engineering design of the landfill soil cover and the evaluation of its air-sealing performance.

In the current gas permeability test methods for unsaturated soil layers, soil samples are mainly obtained at the engineering site and then are transferred to the laboratory to test the gas diffusion coefficient and permeability coefficient of the samples according to Fick's law and Darcy's law, respectively. However, the soil cover of the landfill is widely distributed, the number of soil samples required for testing is huge. Therefore, it is time-consuming and laborious to send the samples to the laboratory for testing, and the soil samples are easily disturbed during transportation. The whole process is complicated and there are many interference factors. Scholars have proposed some in situ testing methods for the gas permeability coefficient of unsaturated soil. Some of these methods require high testing costs, and the other require complex numerical analysis or are affected by empirical coefficients. All these methods have high application thresholds and are difficult to be widely used in engineering.

SUMMARY

In order to overcome the shortcomings in the related art, the disclosure provides a device and a method for in situ penetration measurement of gas transport parameters in an unsaturated soil layer, the transport parameters include a diffusion coefficient and a permeability coefficient and are configured to satisfy engineering application needs.

The disclosure includes the following technical solutions.

1. A device for in situ penetration measurement of gas transport parameters in an unsaturated soil layer is provided.

The device is formed by a gas supply system, a gas concentration display recorder, a gas pressure display recorder, a sleeve, a gas concentration sensor, a gas pressure sensor, a porous gas-permeable tube, and a conical penetration head. A top portion of the porous gas-permeable tube is connected to a bottom portion of the sleeve through threads, a bottom portion of the porous gas-permeable tube is connected to the conical penetration head through threads, and an inner portion of the porous gas-permeable tube is filled with sand grains. The gas supply system includes a high-purity inert gas cylinder, a high-pressure air cylinder, a small-flow pressure regulating valve, a large-flow pressure regulating valve, a small-scale air gauge, a large-scale air gauge, a small-scale mass flow controller, a large-scale mass flow controller, and a gas pipeline. Further, the gas supply system forms two gas supply lines, one is that an output end of the high-purity inert gas cylinder is connected to one end of the gas pipeline through the small-flow pressure regulating valve, the small-scale air gauge, and the small-scale mass flow controller in sequence. The other one is that an output end of the high-pressure air cylinder is also connected to one end of the gas pipeline through the large-flow pressure regulating valve, the large-scale air gauge, the large-scale mass flow controller in sequence. Another end of the gas pipeline extends into and penetrates the sleeve and communicates with the porous gas-permeable tube at a bottom portion of the sleeve. The gas concentration sensor and the gas pressure sensor are installed in the inner portion of the porous gas-permeable tube. The gas concentration sensor and the gas pressure sensor are respectively connected to the gas concentration display recorder outside the porous gas-permeable tube and the gas pressure display recorder through data lines thereof.

A rigid body formed by the sleeve, the porous gas-permeable tube, and the conical penetration head is inserted into the unsaturated soil layer, and the porous gas-permeable tube is located at a depth in the unsaturated soil layer where the gas transport parameters are required to be measured.

The data line is connected to the gas concentration display recorder outside the porous gas-permeable tube and the gas pressure display recorder after penetrating upwards and out of the sleeve.

The gas concentration sensor and the gas pressure sensor are installed on an inner wall of the porous gas-permeable tube.

A lower portion of the sleeve is disposed in the unsaturated soil layer, and an upper portion extends out of ground.

The gas cylinder includes but not limited to a high-pressure air cylinder and a high-purity inert gas cylinder, and is used to generate the air pressure required for gas introduction and to be used as tracer gas.

The pressure regulating valves and the air gauges are configured to control the air pressure of the gas pipeline, so that the air pressure is within safe ranges allowed by the mass flow controllers.

The small-scale mass flow controller and the large-scale mass flow controller are configured to provide different ranges of constant gas inlet flow.

A length of the sleeve may be adjusted according to a designed depth, including but not limited to using one sleeve, and a plurality of sleeves may be connected by threads.

2. A testing method for in situ penetration measurement of gas transport parameters in an unsaturated soil layer is provided, and the method includes the following steps.

In step one, a gas concentration sensor and a gas pressure sensor are installed on an inner wall of a porous gas-permeable tube, the gas concentration sensor and the gas pressure sensor are connected to a gas concentration display recorder and a gas pressure display recorder through data lines, then, a sleeve, the porous gas-permeable tube, and a conical penetration head are connected in sequence to form a rigid body, and the porous gas-permeable tube is filled with sand grains.

In step two, the porous gas-permeable tube is inserted to a target depth where the gas transport parameters of the unsaturated soil layer need to be measured.

In step three, a high-purity inert gas cylinder, a high-pressure air cylinder, a small-flow pressure regulating valve, a large-flow pressure regulating valve, a small-scale air gauge, a large-scale air gauge, a small-scale mass flow controller, and a large-scale mass flow controller are connected through a gas pipeline to form a gas supply system, and an outlet end of the gas supply system is connected to a top end of the sleeve.

In step four, the small-flow pressure regulating valve is turned on, the large-flow pressure regulating valve is turned off, inert gas is delivered to the porous gas-permeable tube through the gas supply system; then, the gas concentration display recorder and the gas pressure display recorder are turned on; a concentration value and an air pressure value of the inert gas in the porous gas-permeable tube are measured in real time, and an air intake flow is regulated to a constant flow value through the small-scale mass flow controller, such that after a gas concentration measured by the gas concentration sensor is stable, a gas pressure value measured by the gas pressure sensor is equal to an atmospheric pressure value.

In step five, after the reading of the gas concentration display recorder is stable, an inert gas concentration value $C_1$ measured at this time by the gas concentration sensor in the porous gas-permeable tube and a corresponding first air intake flow value $q_{v1}$ controlled by the small-scale mass flow controller are recorded.

In step six: the small-flow pressure regulating valve is turned off, the large-flow pressure regulating valve is turned on, air is delivered to the porous gas-permeable tube through the gas supply system, the air intake flow is increased to a higher constant flow value through the large-scale mass flow controller, such that the gas pressure value measured by the gas pressure sensor is greater than the atmospheric pressure value and exhibits a significant difference (e.g., the difference is greater than 100 Pa), and after reading of the gas pressure display recorder is stable, a gas pressure value $P_2$ measured at this time by the gas pressure sensor in the porous gas-permeable tube and a corresponding second air intake flow value $q_{v2}$ controlled by the large-scale mass flow controller are recorded.

In step seven, the measured inert gas concentration value $C_1$ and the first air intake flow value $q_{v1}$ are substituted into a following formula to obtain a gas diffusion coefficient value D:

$$D = \frac{P_s T_{atm}}{P_{atm} T_s} \frac{q_{v1}}{4\pi r_0 (C_1 - C_{environment})}$$

where D is a gas diffusion coefficient ($m^2\ s^{-1}$) of the unsaturated soil layer; $C_1$ is the concentration value ($m^3\ m^{-3}$) of the inert gas in the porous gas-permeable tube when gas is stably transported; $C_{enviroment}$ is a background concentration value ($m^3\ m^{-3}$) of the inert gas in the soil layer; $r_0$ is a radius (m) of the porous gas-permeable tube; $P_s$ and $T_s$ are the atmospheric pressure (101,325 Pa) and the temperature (273.15 K) under a standard condition, respectively; and $P_{atm}$ and $T_{atm}$ are the ambient atmospheric pressure (Pa) and the ambient temperature (K), respectively.

In step eight, the measured gas pressure value $P_2$ and the second air intake flow value $q_{v2}$ are substituted into a following formula to obtain a gas permeability coefficient $k_a$:

$$k_a = \frac{P_s T_{atm}}{P_{atm} T_s} \frac{P_2 q_{v2} \mu_a}{2\pi r_0 (P_2^2 - P_{atm}^2)}$$

where $k_a$ is the gas permeability coefficient ($m^2$) of the unsaturated soil layer, $\mu_a$ is the viscosity (Pa·s) of air, and $P_2$ is an absolute air pressure value (Pa) in the porous gas-permeable tube.

In the disclosure, the gas diffusion coefficient and the permeability coefficient of the unsaturated soil can be obtained by measuring the gas pressure value, the gas concentration value, and the corresponding gas flow value of the unsaturated soil layer at only one depth (target point position) required to be tested and substituting same into a calculation formula of the gas diffusion coefficient and the permeability coefficient.

Effects provided by the disclosure include the following.

The device and method of the disclosure can measure the gas diffusion coefficient at a specific point in the unsaturated soil layer when the relative air pressure in the cavity of the porous gas-permeable tube is zero and can measure the gas permeability coefficient at this point when the relative air pressure in the cavity is high (e.g., above 100 Pa). Through the mass flow meters, the air intake flow value is regulated to gradually increase from zero. After gas transport in the cavity of the porous gas-permeable tube is stable, the concentration value of the inert gas under the low air intake flow and the air pressure value under the high air intake flow are measured. In this way, the gas diffusion coefficient and permeability coefficient of the unsaturated soil layer at this point can be measured together.

In the disclosure, it is only necessary to measure the inert gas concentration/pressure and the corresponding gas flow at a specific point in the unsaturated soil during the steady-state transport of gas, and then the precise gas diffusion coefficient/permeability coefficient of the unsaturated soil at the point, rather than the average gas diffusion coefficient/permeability coefficient among neighboring regions, can be obtained through simple calculation.

In the disclosure, the relevant parameters of the target point position are measured, so the influences brought by the sidewall dominant flow and the measurement error when measuring the air pressure difference/concentration difference between two points of the soil layer in the conventional method are thereby avoided. The disturbance to the testing results is reduced, and accurate measurement results can be obtained.

Through the device and the method provided by the disclosure, the tedious and time-consuming process of sending samples to the laboratory for testing is avoided, and there is no need to spend an excessive amount of money to build testing facilities on site.

BRIEF DESCRIPTION OF THE DRAWINGS

The following are provided in the figures, 1: high-purity inert gas cylinder, 2: high-pressure air cylinder, 3: small-flow pressure regulating valve, 4: large-flow pressure regulating valve, 5: air gauge, 6: air gauge, 7: small-scale mass flow controller, 8: large-scale mass flow controller, 9: gas pipeline, 10: gas concentration display recorder, 11: gas pressure display recorder, 12: data line, 13: sleeve, 14: gas concentration sensor, 15: gas pressure sensor, 16: porous gas-permeable tube, and 17: conical penetration head.

DESCRIPTION OF THE EMBODIMENTS

The disclosure is further described in detail in combination with accompanying figures and embodiments. It should be pointed out that the description of this embodiment is intended to further explain the disclosure, but is not intended to limit the disclosure.

Figure 1:
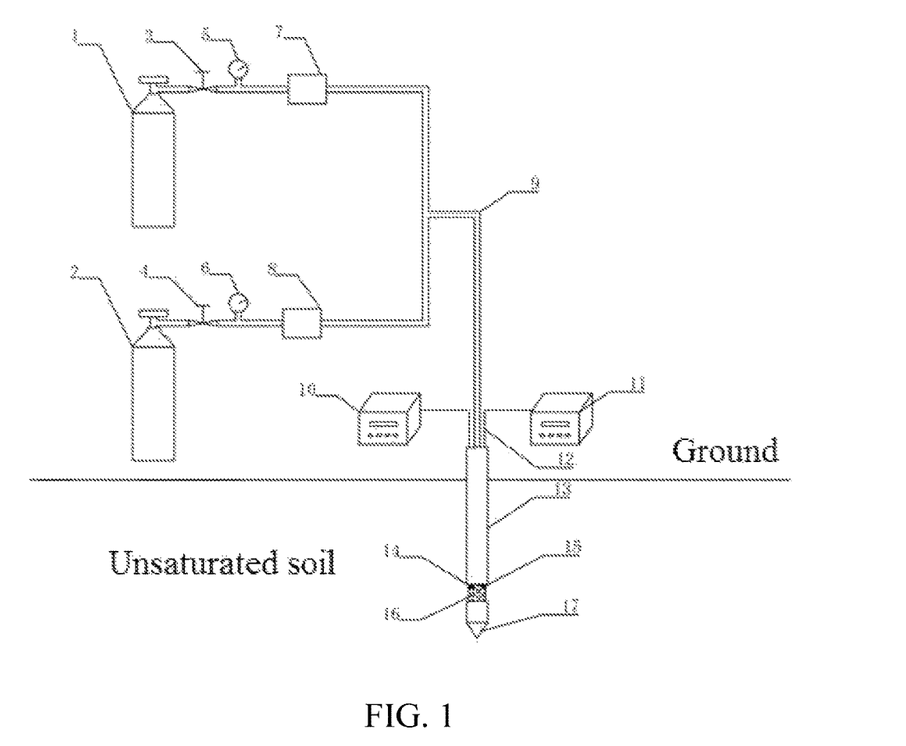
FIG. 1 is a schematic view of a structure of a device according to the disclosure.
Figure 2:
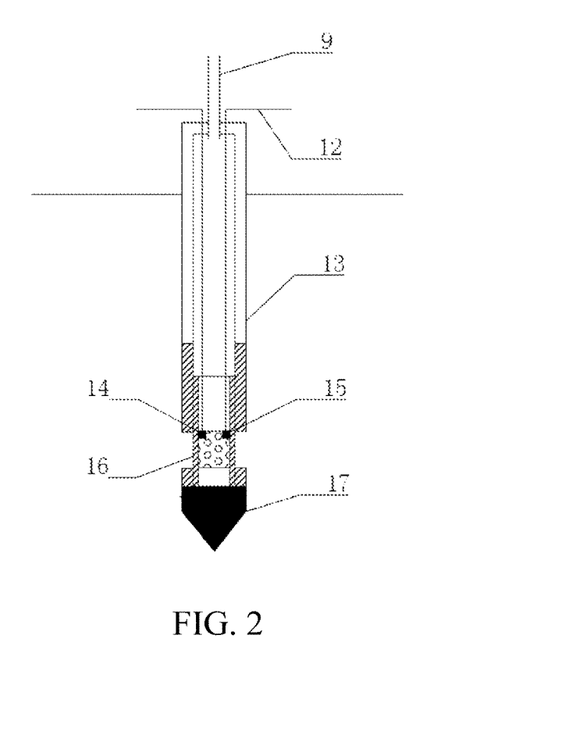
FIG. 2 is a cross-sectional view of a testing device penetrating into a soil layer.
Figure 3:
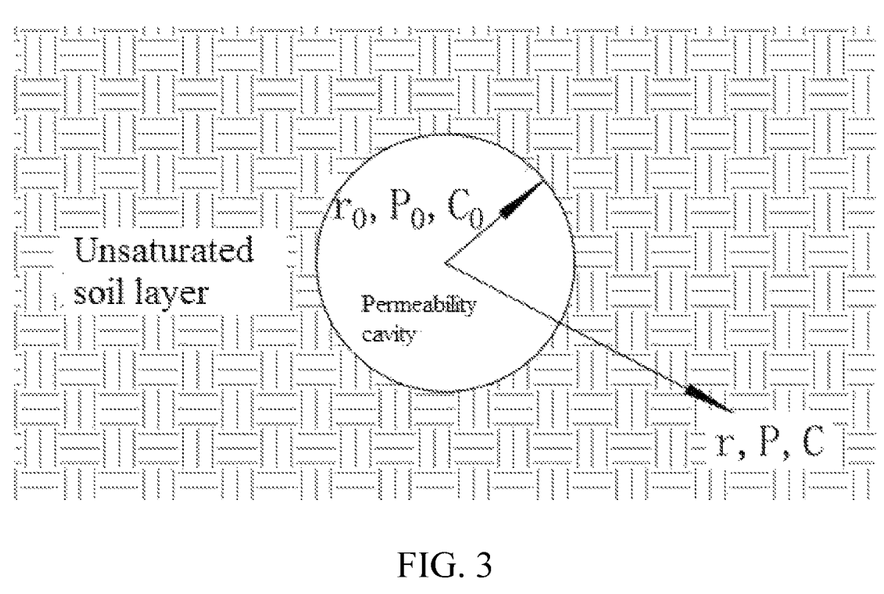
FIG. 3 is a schematic diagram of a one-dimensional steady-state gas transport corresponding to a cavity of a porous gas-permeable tube in an unsaturated soil layer.

As shown in FIG. 1, a gas supply system, a gas concentration display recorder 10, a gas pressure display recorder 11, a sleeve 13, a gas concentration sensor 14, a gas pressure sensor 15, a porous gas-permeable tube 16, and a conical penetration head 17 are included. As shown in FIG. 2, a top portion of the porous gas-permeable tube 16 is connected to a bottom portion of the sleeve 13 through a thread, a bottom portion of the porous gas-permeable tube 16 is connected to the conical penetration head 17 through a thread, and an inner portion of the porous gas-permeable tube 16 is filled with sand grains. A rigid body formed by the sleeve 13, the porous gas-permeable tube 16, and the conical penetration head 17 is inserted into an unsaturated soil layer, and the porous gas-permeable tube 16 is located at a depth in the unsaturated soil layer where gas transport parameters are required to be measured. A lower portion of the sleeve 13 is disposed in the unsaturated soil layer, and an upper portion extends out of the ground.

As shown in FIG. 1, the gas supply system includes a high-purity inert gas cylinder 1, a high-pressure air cylinder 2, a small-flow pressure regulating valve 3, a large-flow pressure regulating valve 4, a small-scale air gauge 5, a large-scale air gauge 6, a small-scale mass flow controller 7, a large-scale mass flow controller 8, and a gas pipeline 9. Further, the gas supply system forms two gas supply lines, one is that an output end of the high-purity inert gas cylinder 1 is connected to one end of the gas pipeline 9 through the small-flow pressure regulating valve 3, the small-scale air gauge 5, and the small-scale mass flow controller 7 in sequence. The other one is that an output end of the high-pressure air cylinder 2 is also connected to one end of the gas pipeline 9 through the large-flow pressure regulating valve 4, the large-scale air gauge 6, the large-scale mass flow controller 8 in sequence. An outlet end of the gas supply system is connected to a top end of the sleeve 13, and another end of the gas pipeline 9 extends into and penetrates the top end of the sleeve 13 and communicates with the porous gas-permeable tube 16 at a bottom portion of the sleeve 13. The gas concentration sensor 14 and the gas pressure sensor 15 are installed on an inner wall of in the inner portion of the porous gas-permeable tube 16. The gas concentration sensor 14 and the gas pressure sensor 15 are respectively connected to the gas concentration display recorder 10 outside the porous gas-permeable tube 16 and the gas pressure display recorder 11 through data lines 12 thereof. The data line 12 is connected to the gas concentration display recorder 10 outside the porous gas-permeable tube 16 and the gas pressure display recorder 11 after penetrating upwards and out of the sleeve 13.

The high-purity inert gas cylinder 1 and the high-pressure air cylinder 2 provide the gas and air pressure delivered to the porous gas-permeable tube 16. The small-scale mass flow controller 7 and the large-scale mass flow controller 8 precisely control the air intake flow. The gas pipe 9 delivers gas. The porous gas-permeable tube 16 acts as a gas transport channel. By filling the porous gas-permeable tube with sand grains, the pores of the porous gas-permeable tube are prevented from being blocked by the soil layer, which may affect a gas transport path. The gas concentration sensor 14 and the gas pressure sensor 15 are respectively connected to the gas concentration display recorder 10 and the gas pressure display recorder 11 to measure the air pressure and gas concentration at a design depth.

Further, a wear-resistant and pressure-resistant PU reinforced pipeline with a diameter of 10 mm is adopted for the gas pipeline 9. The sleeve 13, porous gas-permeable tube 16, and the conical penetration head 17 are made of a cast iron material with high rigidity. An outer diameter and an inner diameter of the sleeve 13 respectively are 5.0 cm and 3.5 cm, an outer diameter and an inner diameter of the porous gas-permeable tube 16 respectively are 3.5 cm and 2 cm, and an outer diameter of the conical penetration head is 5.0 cm. The high-purity inert gas cylinder 1 is a high-purity argon gas cylinder, and the gas concentration sensor 14 is an argon gas sensor. Full-scale flow ranges of the small-scale mass flow controller 7 and the large-scale mass flow controller 8 respectively are 5 SCCM (standard milliliters/minute) and 5 SLM (standard liters/minute) with a control accuracy of ±1.5% F.S. The small-flow pressure regulating valve 3, the large-flow pressure regulating valve 4, the small-scale air gauge 5, the large-scale air gauge 6, the gas concentration display recorder 10, the gas pressure display recorder 11, and the gas pressure sensor 15 all use conventional instruments.

Implementation of the disclosure includes the following steps.

In step one, the gas concentration sensor 14 and the gas pressure sensor 15 are installed on the inner wall of the porous gas-permeable tube 16, the gas concentration sensor 14 and the gas pressure sensor 15 are connected to the gas concentration display recorder 10 and the gas pressure display recorder 11 through the data lines 12, the sleeve 13, the porous gas-permeable tube 16, and the conical penetration head 17 are connected in sequence to form a rigid body, and the porous gas-permeable tube 16 is filled with sand grains.

In step two, the porous gas-permeable tube 16 is inserted to a depth of the unsaturated soil layer required to be tested, and the depth is 0.6 meters.

In step three, the high-purity argon gas cylinder 1, the high-pressure air cylinder 2, the small-flow pressure regulating valve 3, the large-flow pressure regulating valve 4, the small-scale air gauge 5, the large-scale air gauge 6, the small-scale mass flow controller 7, and the large-scale mass flow controller 8 are connected through the gas pipeline 9 to form the gas supply system, and the outlet end of the gas supply system is connected to the top end of the sleeve 13.

In step four, the small-flow pressure regulating valve 3 is turned on, the large-flow pressure regulating valve 4 is turned off, high-purity argon gas is delivered to the porous gas-permeable tube 16 through the gas supply system, the gas concentration display recorder 10 and the gas pressure display recorder 11 are turned on, a concentration value and an air pressure value of the argon gas in the porous gas-permeable tube 16 are measured in real time, and an air intake flow is regulated through the small-scale mass flow controller 7 to a constant flow value, such that after a gas concentration of the argon gas measured by the gas concentration sensor 14 is stable, a gas pressure value in the porous gas-permeable tube 16 measured by the gas pressure sensor 15 is equal to an atmospheric pressure value.

In step five, after reading of the gas concentration display recorder 10 is stable, a concentration value $C_1$ (0.124 m³ m⁻³) of the argon gas measured at this time by the gas concentration sensor 14 in the porous gas-permeable tube 16 and a corresponding first air intake flow value $q_{v1}$ (2.0 SCCM) controlled by the small-scale mass flow controller 6 are recorded.

In step six, the small-flow pressure regulating valve 3 is turned off, the large-flow pressure regulating valve 4 is turned on, air is delivered to the porous gas-permeable tube 16 through the gas supply system, the air intake flow is increased to a higher constant flow value through the large-scale mass flow controller 8, such that the gas pressure value in the porous gas-permeable tube 16 measured by the gas pressure sensor 15 is greater than the atmospheric pressure value and exhibits a relative air pressure difference value exceeding 100 Pa, and after reading of the gas pressure display recorder 11 is stable, a gas pressure value $P_2$ (94,420 Pa) measured at this time by the gas pressure sensor 15 in the porous gas-permeable tube 16 and a corresponding second air intake flow value $q_{v2}$ (1.0 SLM) controlled by the large-scale mass flow controller 8 are recorded.

In step seven: the measured argon gas concentration value $C_1$ and the first air intake flow value $q_{v1}$ are substituted into a following formula to obtain a gas diffusion coefficient value D:

$$D = \frac{P_s T_{atm}}{P_{atm} T_s} \frac{q_{v1}}{4\pi r_0 (C_1 - C_{environment})}$$

$$= \frac{101325 \times 298.15}{94000 \times 273.15} \times \frac{2 \times 10^{-6}}{60 \times 4 \times 3.14 \times 0.0175 \times 0.124}$$

$$= 1.439 \times 10^{-6} m^2 s^{-1}$$

where D is a gas diffusion coefficient (m² s⁻¹) of the unsaturated soil layer, $q_{v1}$ is the first air intake flow value (m³ s⁻¹) controlled by the small-scale mass flow controller 7, $C_1$ is the concentration value (m³ m⁻³) of the argon gas in the porous gas-permeable tube 16 when gas is stably transported, $C_{environment}$ is a background concentration value of argon gas in the soil layer (the argon concentration in the air is 0 m³ m⁻³ here), $r_0$ is a radius (0.0175 m) of the porous gas-permeable tube 16, $P_s$ and $T_s$ respectively are an atmospheric pressure (101,325 Pa) and a temperature (273.15 K) under a standard condition, and $P_{atm}$ and $T_{atm}$ respectively are an ambient atmospheric pressure (94,000 Pa) and an ambient temperature (298.15K).

In step eight, the measured gas pressure value $P_2$ and the second air intake flow value $q_{v2}$ are substituted into a following formula to obtain a gas permeability coefficient $k_a$:

$$k_a = \frac{P_s T_{atm}}{P_{atm} T_s} \frac{P_2 q_{v2} \mu_a}{2\pi r_0 (P_2^2 - P_{atm}^2)}$$

$$= \frac{101325 \times 298.15}{94000 \times 273.15} \times \frac{94420 \times 1 \times 10^{-3} \times 1.84 \times 10^{-5}}{60 \times 2 \times 3.14 \times 0.0175 \times (94420^2 - 94000^2)}$$

$$= 3.917 \times 10^{-12} m^2$$

where $k_a$ is the gas permeability coefficient (m²) of the unsaturated soil layer, $q_{v2}$ is the second air intake flow value (m³ s⁻¹) controlled by the large-scale mass flow controller 8, $\mu_a$ is the viscosity (1.84×10−5 Pa·s here) of air, and $P_2$ is an absolute air pressure value (Pa) in the porous gas-permeable tube 16.

Based on the above implementation, it can be seen that the testing process provided by the disclosure is simple and fast. The gas permeability coefficient/diffusion coefficient of unsaturated soil of a position can be obtained by only testing the gas pressure/gas concentration value and the corresponding gas flow value at the point position of the designed depth through simple calculation. Compared to the related art, the testing process is low in costs and is simple in operation and convenient in calculation. The gas diffusion coefficient and the permeability coefficient of an unsaturated soil layer may be quickly and accurately measured at the designed depth on site, and high engineering application value is thereby provided.

What is claimed is:

1. A device for in situ penetration measurement of gas transport parameters in an unsaturated soil layer, comprising:

a gas supply system, a gas concentration display recorder, a gas pressure display recorder, a sleeve, a gas concentration sensor, a gas pressure sensor, a porous gas-permeable tube, and a conical penetration head, wherein a top portion of the porous gas-permeable tube is connected to a bottom portion of the sleeve through a thread, a bottom portion of the porous gas-permeable tube is connected to the conical penetration head through a thread, an inner portion of the porous gas-permeable tube is filled with sand grains, the gas supply system comprises a high-purity inert gas cylinder, a high-pressure air cylinder, a small-flow pressure regulating valve, a large-flow pressure regulating valve, a small-scale air gauge, a large-scale air gauge, a small-scale mass flow controller, a large-scale mass flow controller, and a gas pipeline, an output end of the high-purity inert gas cylinder is connected to one end of the gas pipeline through the small-flow pressure regulating valve, the small-scale air gauge, and the small-scale mass flow controller in sequence, an output end of the high-pressure air cylinder is also connected to one end of the gas pipeline through the large-flow pressure regulating valve, the large-scale air gauge, the large-scale mass flow controller in sequence, another end of the gas pipeline extends into and penetrates the sleeve and communicates with the porous gas-permeable tube at a bottom portion of the sleeve; the gas concentration sensor and the gas pressure sensor are installed in the inner portion of the porous gas-permeable tube, and the gas concentration sensor and the gas pressure sensor are respectively connected to the gas concentration display recorder outside the porous gas-permeable tube and the gas pressure display recorder through data lines thereof.

2. The device for in situ penetration measurement of gas transport parameters in the unsaturated soil layer according to claim 1, wherein a rigid body formed by the sleeve, the porous gas-permeable tube, and the conical penetration head is inserted into the unsaturated soil layer, and the porous gas-permeable tube is located at a depth in the unsaturated soil layer where the gas transport parameters are required to be measured.

3. A testing method for in situ penetration measurement of gas transport parameters in an unsaturated soil layer applied in the device according to claim 2, comprising:

step one: installing the gas concentration sensor and the gas pressure sensor on the inner wall of the porous gas-permeable tube, connecting, by the data lines, the gas concentration sensor and the gas pressure sensor to the gas concentration display recorder and the gas pressure display recorder, connecting the sleeve, the porous gas-permeable tube, and the conical penetration head in sequence to form a rigid body, filling the porous gas-permeable tube with sand grains;

step two: inserting the porous gas-permeable tube to a depth of the unsaturated soil layer required to be tested;

step three: connecting, through the gas pipeline, the high-purity inert gas cylinder, the high-pressure air cylinder, the small-flow pressure regulating valve, the large-flow pressure regulating valve, the small-scale air gauge, the large-scale air gauge, the small-scale mass flow controller, and the large-scale mass flow controller to form the gas supply system, wherein an outlet end of the gas supply system is connected to a top end of the sleeve;

step four: turning on the small-flow pressure regulating valve, turning off the large-flow pressure regulating valve, delivering, through the gas supply system, inert gas to the porous gas-permeable tube, turning on the gas concentration display recorder and the gas pressure display recorder, measuring a concentration value and an air pressure value of the inert gas in the porous gas-permeable tube in real time, and regulating, through the small-scale mass flow controller, an air intake flow to a constant flow value, such that after a gas concentration measured by the gas concentration sensor is stable, a gas pressure value measured by the gas pressure sensor is equal to an atmospheric pressure value;

step five: recording an inert gas concentration value $C_1$ measure at this timed by the gas concentration sensor in the porous gas-permeable tube and a corresponding first air intake flow value $q_{v1}$ of the small-scale mass flow controller after reading of the gas concentration display recorder is stable;

step six: turning off the small-flow pressure regulating valve, turning on the large-flow pressure regulating valve, delivering, through the gas supply system, air to the porous gas-permeable tube, increasing, through the large-scale mass flow controller, the air intake flow to a higher constant flow value, such that the gas pressure value measured by the gas pressure sensor is greater than the atmospheric pressure value and exhibits a significant difference, and recording a gas pressure value $P_2$ measured at this time by the gas pressure sensor in the porous gas-permeable tube and a corresponding second air intake flow value $q_{v2}$ of the large-scale mass flow controller after reading of the gas pressure display recorder is stable;

step seven: substituting the measured inert gas concentration value $C_1$ and the first air intake flow value $q_{v1}$ into a following formula to obtain a gas diffusion coefficient value D:

$$D = \frac{P_s T_{atm}}{P_{atm} T_s} \frac{q_{v1}}{4\pi r_0 (C_1 - C_{environment})}$$

wherein D is a gas diffusion coefficient of the unsaturated soil layer, $C_1$ is the concentration value of the inert gas in the porous gas-permeable tube when gas is stably transported, $C_{enviroment}$ is a background concentration value of the inert gas in the soil layer, $r_0$ is a radius of the porous gas-permeable tube, $P_s$ and $T_s$ respectively are an atmospheric pressure and a temperature under a standard condition, and $P_{atm}$ and $T_{atm}$ respectively are an ambient atmospheric pressure and an ambient temperature; and step eight: substituting the measured gas pressure value $P_2$ and the second air intake flow value $q_{v2}$ into a following formula to obtain a gas permeability coefficient $k_a$:

$$k_a = \frac{P_s T_{atm}}{P_{atm} T_s} \frac{P_2 q_{v2} \mu_a}{2\pi r_0 (P_2^2 - P_{atm}^2)}$$

wherein $k_a$ is the gas permeability coefficient of the unsaturated soil layer, $\mu_a$ is a viscosity of air, and $P_2$ is an absolute air pressure value in the porous gas-permeable tube.

4. The device for in situ penetration measurement of gas transport parameters in the unsaturated soil layer according to claim 1, wherein the data line is connected to the gas concentration display recorder outside the porous gas-permeable tube and the gas pressure display recorder after penetrating upwards and out of the sleeve.

5. A testing method for in situ penetration measurement of gas transport parameters in an unsaturated soil layer applied in the device according to claim 4, comprising:

step one: installing the gas concentration sensor and the gas pressure sensor on the inner wall of the porous gas-permeable tube, connecting, by the data lines, the gas concentration sensor and the gas pressure sensor to the gas concentration display recorder and the gas pressure display recorder, connecting the sleeve, the porous gas-permeable tube, and the conical penetration head in sequence to form a rigid body, filling the porous gas-permeable tube with sand grains;

step two: inserting the porous gas-permeable tube to a depth of the unsaturated soil layer required to be tested;

step three: connecting, through the gas pipeline, the high-purity inert gas cylinder, the high-pressure air cylinder, the small-flow pressure regulating valve, the large-flow pressure regulating valve, the small-scale air gauge, the large-scale air gauge, the small-scale mass flow controller, and the large-scale mass flow controller to form the gas supply system, wherein an outlet end of the gas supply system is connected to a top end of the sleeve;

step four: turning on the small-flow pressure regulating valve, turning off the large-flow pressure regulating valve, delivering, through the gas supply system, inert gas to the porous gas-permeable tube, turning on the gas concentration display recorder and the gas pressure display recorder, measuring a concentration value and an air pressure value of the inert gas in the porous gas-permeable tube in real time, and regulating, through the small-scale mass flow controller, an air intake flow to a constant flow value, such that after a gas concentration measured by the gas concentration sensor is stable, a gas pressure value measured by the gas pressure sensor is equal to an atmospheric pressure value;

step five: recording an inert gas concentration value $C_1$ measure at this timed by the gas concentration sensor in the porous gas-permeable tube and a corresponding first air intake flow value $qv_1$ of the small-scale mass flow controller after reading of the gas concentration display recorder is stable;

step six: turning off the small-flow pressure regulating valve, turning on the large-flow pressure regulating valve, delivering, through the gas supply system, air to the porous gas-permeable tube, increasing, through the large-scale mass flow controller, the air intake flow to a higher constant flow value, such that the gas pressure value measured by the gas pressure sensor is greater than the atmospheric pressure value and exhibits a significant difference, and recording a gas pressure value $P_2$ measured at this time by the gas pressure sensor in the porous gas-permeable tube and a corresponding second air intake flow value $qv_2$ of the large-scale mass flow controller after reading of the gas pressure display recorder is stable;

step seven: substituting the measured inert gas concentration value $C_1$ and the first air intake flow value $q_{v1}$ into a following formula to obtain a gas diffusion coefficient value D:

$$D = \frac{P_s T_{atm}}{P_{atm} T_s} \frac{q_{v1}}{4\pi r_0 (C_1 - C_{environment})}$$

wherein D is a gas diffusion coefficient of the unsaturated soil layer, $C_1$ is the concentration value of the inert gas in the porous gas-permeable tube when gas is stably transported, $C_{enviroment}$ is a background concentration value of the inert gas in the soil layer, $r_0$ is a radius of the porous gas-permeable tube, $P_s$ and $T_s$ respectively are an atmospheric pressure and a temperature under a standard condition, and $P_{atm}$ and $T_{atm}$ respectively are an ambient atmospheric pressure and an ambient temperature; and step eight: substituting the measured gas pressure value $P_2$ and the second air intake flow value $q_{v2}$ into a following formula to obtain a gas permeability coefficient $k_a$:

$$k_a = \frac{P_s T_{atm}}{P_{atm} T_s} \frac{P_2 q_{v2} \mu_a}{2\pi r_0 (P_2^2 - P_{atm}^2)}$$

wherein $k_a$ is the gas permeability coefficient of the unsaturated soil layer, $\mu_a$ is a viscosity of air, and $P_2$ is an absolute air pressure value in the porous gas-permeable tube.

6. The device for in situ penetration measurement of gas transport parameters in the unsaturated soil layer according to claim 1, wherein the gas concentration sensor and the gas pressure sensor are installed on an inner wall of the porous gas-permeable tube.

7. A testing method for in situ penetration measurement of gas transport parameters in an unsaturated soil layer applied in the device according to claim 6, comprising:

step one: installing the gas concentration sensor and the gas pressure sensor on the inner wall of the porous gas-permeable tube, connecting, by the data lines, the gas concentration sensor and the gas pressure sensor to the gas concentration display recorder and the gas pressure display recorder, connecting the sleeve, the porous gas-permeable tube, and the conical penetration head in sequence to form a rigid body, filling the porous gas-permeable tube with sand grains;

step two: inserting the porous gas-permeable tube to a depth of the unsaturated soil layer required to be tested;

step three: connecting, through the gas pipeline, the high-purity inert gas cylinder, the high-pressure air cylinder, the small-flow pressure regulating valve, the large-flow pressure regulating valve, the small-scale air gauge, the large-scale air gauge, the small-scale mass flow controller, and the large-scale mass flow controller to form the gas supply system, wherein an outlet end of the gas supply system is connected to a top end of the sleeve;

step four: turning on the small-flow pressure regulating valve, turning off the large-flow pressure regulating valve, delivering, through the gas supply system, inert gas to the porous gas-permeable tube, turning on the gas concentration display recorder and the gas pressure display recorder, measuring a concentration value and an air pressure value of the inert gas in the porous gas-permeable tube in real time, and regulating, through the small-scale mass flow controller, an air intake flow to a constant flow value, such that after a gas concentration measured by the gas concentration sensor is stable, a gas pressure value measured by the gas pressure sensor is equal to an atmospheric pressure value;

step five: recording an inert gas concentration value $C_1$ measure at this timed by the gas concentration sensor in the porous gas-permeable tube and a corresponding first air intake flow value $qv_1$ of the small-scale mass flow controller after reading of the gas concentration display recorder is stable;

step six: turning off the small-flow pressure regulating valve, turning on the large-flow pressure regulating valve, delivering, through the gas supply system, air to the porous gas-permeable tube, increasing, through the large-scale mass flow controller, the air intake flow to a higher constant flow value, such that the gas pressure value measured by the gas pressure sensor is greater than the atmospheric pressure value and exhibits a significant difference, and recording a gas pressure value $P_2$ measured at this time by the gas pressure sensor in the porous gas-permeable tube and a corresponding second air intake flow value $q_{v2}$ of the large-scale mass flow controller after reading of the gas pressure display recorder is stable;

step seven: substituting the measured inert gas concentration value $C_1$ and the first air intake flow value $q_{v1}$ into a following formula to obtain a gas diffusion coefficient value D:

$$D = \frac{P_s T_{atm}}{P_{atm} T_s} \frac{q_{v1}}{4\pi r_0 (C_1 - C_{environment})}$$

wherein D is a gas diffusion coefficient of the unsaturated soil layer, $C_1$ is the concentration value of the inert gas in the porous gas-permeable tube when gas is stably transported, $C_{enviroment}$ is a background concentration value of the inert gas in the soil layer, $r_0$ is a radius of the porous gas-permeable tube, $P_s$ and $T_s$ respectively are an atmospheric pressure and a temperature under a standard condition, and $P_{atm}$ and $T_{atm}$ respectively are an ambient atmospheric pressure and an ambient temperature; and step eight: substituting the measured gas pressure value $P_2$ and the second air intake flow value $q_{v2}$ into a following formula to obtain a gas permeability coefficient $k_a$:

$$k_a = \frac{P_s T_{atm}}{P_{atm} T_s} \frac{P_2 q_{v2} \mu_a}{2\pi r_0 (P_2^2 - P_{atm}^2)}$$

wherein $k_a$ is the gas permeability coefficient of the unsaturated soil layer, $\mu_a$ is a viscosity of air, and $P_2$ is an absolute air pressure value in the porous gas-permeable tube.

8. The device for in situ penetration measurement of gas transport parameters in the unsaturated soil layer according to claim 1, wherein a lower portion of the sleeve is disposed in the unsaturated soil layer, and an upper portion extends out of ground.

9. A testing method for in situ penetration measurement of gas transport parameters in an unsaturated soil layer applied in the device according to claim 8, comprising:

step one: installing the gas concentration sensor and the gas pressure sensor on the inner wall of the porous gas-permeable tube, connecting, by the data lines, the gas concentration sensor and the gas pressure sensor to the gas concentration display recorder and the gas pressure display recorder, connecting the sleeve, the porous gas-permeable tube, and the conical penetration head in sequence to form a rigid body, filling the porous gas-permeable tube with sand grains;

step two: inserting the porous gas-permeable tube to a depth of the unsaturated soil layer required to be tested;

step three: connecting, through the gas pipeline, the high-purity inert gas cylinder, the high-pressure air cylinder, the small-flow pressure regulating valve, the large-flow pressure regulating valve, the small-scale air gauge, the large-scale air gauge, the small-scale mass flow controller, and the large-scale mass flow controller to form the gas supply system, wherein an outlet end of the gas supply system is connected to a top end of the sleeve;

step four: turning on the small-flow pressure regulating valve, turning off the large-flow pressure regulating valve, delivering, through the gas supply system, inert gas to the porous gas-permeable tube, turning on the gas concentration display recorder and the gas pressure display recorder, measuring a concentration value and an air pressure value of the inert gas in the porous gas-permeable tube in real time, and regulating, through the small-scale mass flow controller, an air intake flow to a constant flow value, such that after a gas concentration measured by the gas concentration sensor is stable, a gas pressure value measured by the gas pressure sensor is equal to an atmospheric pressure value;

step five: recording an inert gas concentration value $C_1$ measure at this timed by the gas concentration sensor in the porous gas-permeable tube and a corresponding first air intake flow value $q_{v1}$ of the small-scale mass flow controller after reading of the gas concentration display recorder is stable;

step six: turning off the small-flow pressure regulating valve, turning on the large-flow pressure regulating valve, delivering, through the gas supply system, air to the porous gas-permeable tube, increasing, through the large-scale mass flow controller, the air intake flow to a higher constant flow value, such that the gas pressure value measured by the gas pressure sensor is greater than the atmospheric pressure value and exhibits a significant difference, and recording a gas pressure value $P_2$ measured at this time by the gas pressure sensor in the porous gas-permeable tube and a corresponding second air intake flow value $q_{v2}$ of the large-scale mass flow controller after reading of the gas pressure display recorder is stable;

step seven: substituting the measured inert gas concentration value $C_1$ and the first air intake flow value $q_{v1}$ into a following formula to obtain a gas diffusion coefficient value D:

$$D = \frac{P_s T_{atm}}{P_{atm} T_s} \frac{q_{v1}}{4\pi r_0 (C_1 - C_{environment})}$$

wherein D is a gas diffusion coefficient of the unsaturated soil layer, $C_1$ is the concentration value of the inert gas in the porous gas-permeable tube when gas is stably transported, $C_{enviroment}$ is a background concentration value of the inert gas in the soil layer, $r_0$ is a radius of the porous gas-permeable tube, $P_s$ and $T_s$ respectively are an atmospheric pressure and a temperature under a standard condition, and $P_{atm}$ and $T_{atm}$ respectively are an ambient atmospheric pressure and an ambient temperature; and step eight: substituting the measured gas pressure value $P_2$ and the second air intake flow value $q_{v2}$ into a following formula to obtain a gas permeability coefficient $k_a$:

$$k_a = \frac{P_s T_{atm}}{P_{atm} T_s} \frac{P_2 q_{v2} \mu_a}{2\pi r_0 (P_2^2 - P_{atm}^2)}$$

wherein $k_a$ is the gas permeability coefficient of the unsaturated soil layer, $\mu_a$ is a viscosity of air, and $P_2$ is an absolute air pressure value in the porous gas-permeable tube.

10. A testing method for in situ penetration measurement of gas transport parameters in an unsaturated soil layer applied in the device according to claim 1, comprising:

step one: installing the gas concentration sensor and the gas pressure sensor on the inner wall of the porous gas-permeable tube, connecting, by the data lines, the gas concentration sensor and the gas pressure sensor to the gas concentration display recorder and the gas pressure display recorder, connecting the sleeve, the porous gas-permeable tube, and the conical penetration head in sequence to form a rigid body, filling the porous gas-permeable tube with sand grains;

step two: inserting the porous gas-permeable tube to a depth of the unsaturated soil layer required to be tested;

step three: connecting, through the gas pipeline, the high-purity inert gas cylinder, the high-pressure air cylinder, the small-flow pressure regulating valve, the large-flow pressure regulating valve, the small-scale air gauge, the large-scale air gauge, the small-scale mass flow controller, and the large-scale mass flow controller to form the gas supply system, wherein an outlet end of the gas supply system is connected to a top end of the sleeve;

step four: turning on the small-flow pressure regulating valve, turning off the large-flow pressure regulating valve, delivering, through the gas supply system, inert gas to the porous gas-permeable tube, turning on the gas concentration display recorder and the gas pressure display recorder, measuring a concentration value and an air pressure value of the inert gas in the porous gas-permeable tube in real time, and regulating, through the small-scale mass flow controller, an air intake flow to a constant flow value, such that after a gas concentration measured by the gas concentration sensor is stable, a gas pressure value measured by the gas pressure sensor is equal to an atmospheric pressure value;

step five: recording an inert gas concentration value $C_1$ measure at this timed by the gas concentration sensor in the porous gas-permeable tube and a corresponding first air intake flow value $q_{v1}$ of the small-scale mass flow controller after reading of the gas concentration display recorder is stable;

step six: turning off the small-flow pressure regulating valve, turning on the large-flow pressure regulating valve, delivering, through the gas supply system, air to the porous gas-permeable tube, increasing, through the large-scale mass flow controller, the air intake flow to a higher constant flow value, such that the gas pressure value measured by the gas pressure sensor is greater than the atmospheric pressure value and exhibits a significant difference, and recording a gas pressure value $P_2$ measured at this time by the gas pressure sensor in the porous gas-permeable tube and a corresponding second air intake flow value $q_{v2}$ of the large-scale mass flow controller after reading of the gas pressure display recorder is stable;

step seven: substituting the measured inert gas concentration value $C_1$ and the first air intake flow value $q_{v1}$ into a following formula to obtain a gas diffusion coefficient value D:

$$D = \frac{P_s T_{atm}}{P_{atm} T_s} \frac{q_{v1}}{4\pi r_0 (C_1 - C_{environment})}$$

wherein D is a gas diffusion coefficient of the unsaturated soil layer, $C_1$ is the concentration value of the inert gas in the porous gas-permeable tube when gas is stably transported, $C_{environment}$ is a background concentration value of the inert gas in the soil layer, $r_0$ is a radius of the porous gas-permeable tube, $P_s$ and $T_s$ respectively are an atmospheric pressure and a temperature under a standard condition, and $P_{atm}$ and $T_{atm}$ respectively are an ambient atmospheric pressure and an ambient temperature; and step eight: substituting the measured gas pressure value $P_2$ and the second air intake flow value $q_{v2}$ into a following formula to obtain a gas permeability coefficient $k_a$:

$$k_a = \frac{P_s T_{atm}}{P_{atm} T_s} \frac{P_2 q_{v2} \mu_a}{2\pi r_0 (P_2^2 - P_{atm}^2)}$$

wherein $k_a$ is the gas permeability coefficient of the unsaturated soil layer, $\mu_a$ is a viscosity of air, and $P_2$ is an absolute air pressure value in the porous gas-permeable tube.

* * * * *